US00PP32030P3

(12) United States Plant Patent
Giacomelli et al.

(10) Patent No.: US PP32,030 P3
(45) Date of Patent: Aug. 4, 2020

(54) RASPBERRY PLANT NAMED 'TITANIA'

(50) Latin Name: *Rubus idaeus* L.
Varietal Denomination: Titania

(71) Applicant: SANT'ORSOLA SOCIETA' COOPERATIVA AGRICOLA, Pergine Valsugana (IT)

(72) Inventors: Sara Giacomelli, Vigolo Vattaro (IT); Marco Giacomelli, Vigolo Vattaro (IT); Alessandra Viliotti, Vigolo Vattaro (IT)

(73) Assignee: SANT'ORSOLA SOCIETA' COOPERATIVA AGRICOLA, Pergine Valsugana (IT)

( * ) Notice: Subject to any disclaimer, the term of this patent is extended or adjusted under 35 U.S.C. 154(b) by 0 days.

(21) Appl. No.: 16/350,826

(22) Filed: Jan. 18, 2019

(65) Prior Publication Data

US 2019/0223339 P1 Jul. 18, 2019

(30) Foreign Application Priority Data

Jan. 18, 2018 (EP) ..... 20180035

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./156, 203, 204
See application file for complete search history.

*Primary Examiner* — Susan McCormick Ewoldt
(74) *Attorney, Agent, or Firm* — Pepper Hamilton LLP

(57) ABSTRACT

A new a primocane raspberry cultivar named 'Titania' which produces berries which are of a very large size with a good colour and flavour is disclosed. The new cultivar has the advantages of producing two crops per year, where the fruits mainly ripen on current season's cane in autumn.

4 Drawing Sheets

Genus and species: *Rubus idaeus* L.
Variety denomination: 'Titania'.

BACKGROUND OF THE NEW VARIETY

A new and distinct cultivar of red raspberry (*Rubus idaeus* L.) hereinafter referred to by the cultivar denomination 'Titania' is disclosed. The new variety 'Titania' was obtained from the controlled cross between the varieties 'Vajolet Plus' (mother plant) (U.S. Plant Pat. No. 25,573) and the pollen of a wild mountain raspberry plant (father plant) (not patented).

The crossing for the new cultivar occurred in year 2009 in Altopiano della Vigolana (Trento-Italy) and it was subjected to selection in 2010, and successively tested until 2017. The characteristics of the new cultivar have been found stable and have been transmitted without change through succeeding (more than 7 years) asexual propagations by root cutting.

Plant breeder's rights were applied for with the European Union on Jan. 18, 2018. 'Titania' has not been made publicly available.

SUMMARY OF THE INVENTION

The most outstanding and distinguishing characteristics of the cultivar 'Titania' are hereunder reported.

Primocane raspberry plant;
Very vigorous and healthy plant;
Very large fruit size;
Good fruit colour and flavour.

The new variety produces two crops per year and the fruits mainly ripen on current season's cane in autumn.

The new variety can be propagated by: the use of suckers produced in a spawn-bed, root cutting and use of tissue culture techniques. The root cutting is to be preferred.

BRIEF DESCRIPTION OF THE PHOTOGRAPHS

The new red raspberry cultivar 'Titania' is illustrated by the accompanying photographs showing typical specimens of the new variety in colour as true as reasonably possible to make the same colour illustrations of this character by conventional photographic procedures. The photographs are of plants that are from four to six months old.

DETAILED DESCRIPTION

Figure 1:
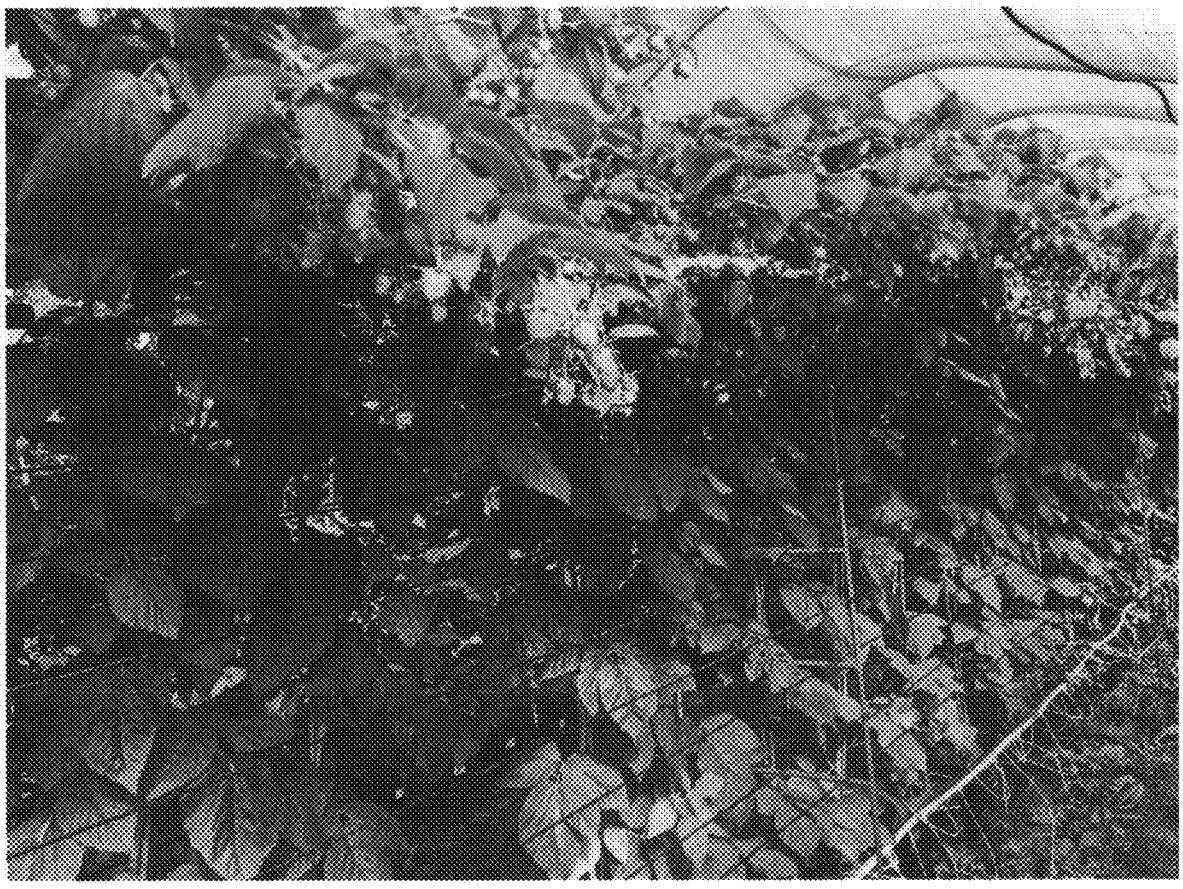
FIG. 1 is a view showing the raspberry plant with growing fruits. The upright and tall plants with very vigorous lateral shoots, mainly present on the apical part of the plant, can be appreciated.
Figure 2:
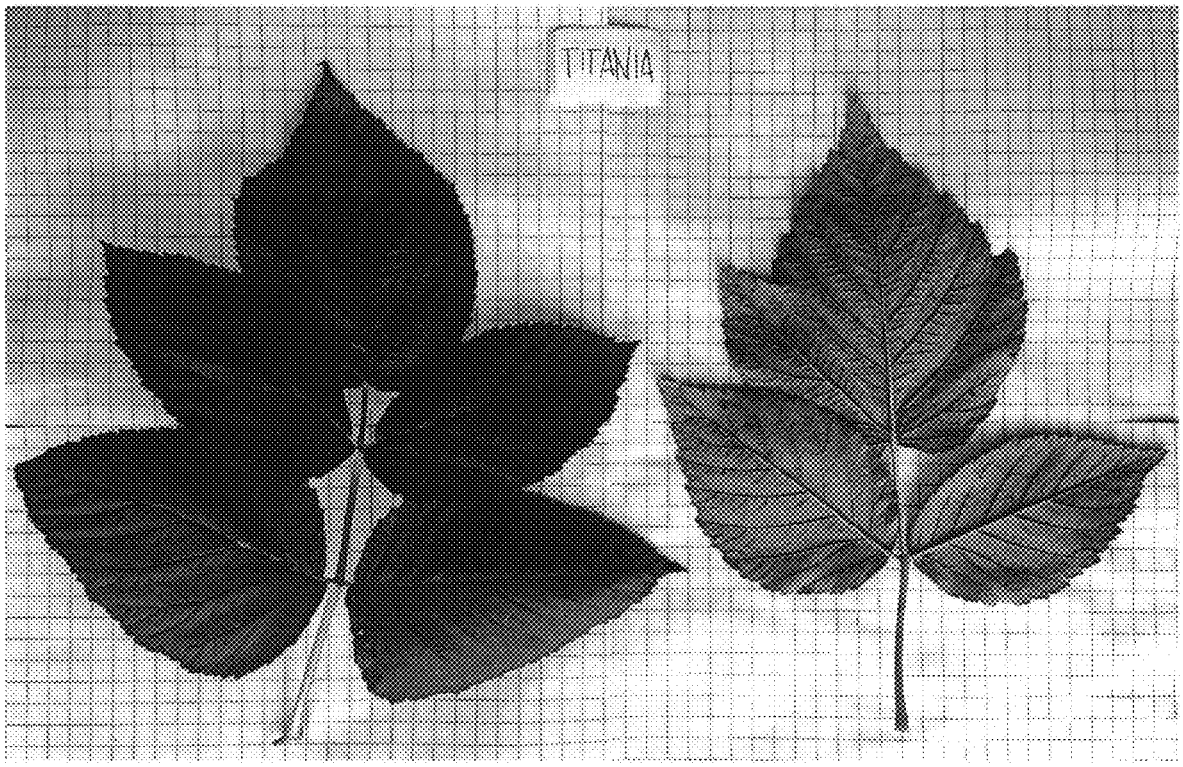
FIG. 2 is a view showing the leaf upper and lower surfaces.
Figure 3:
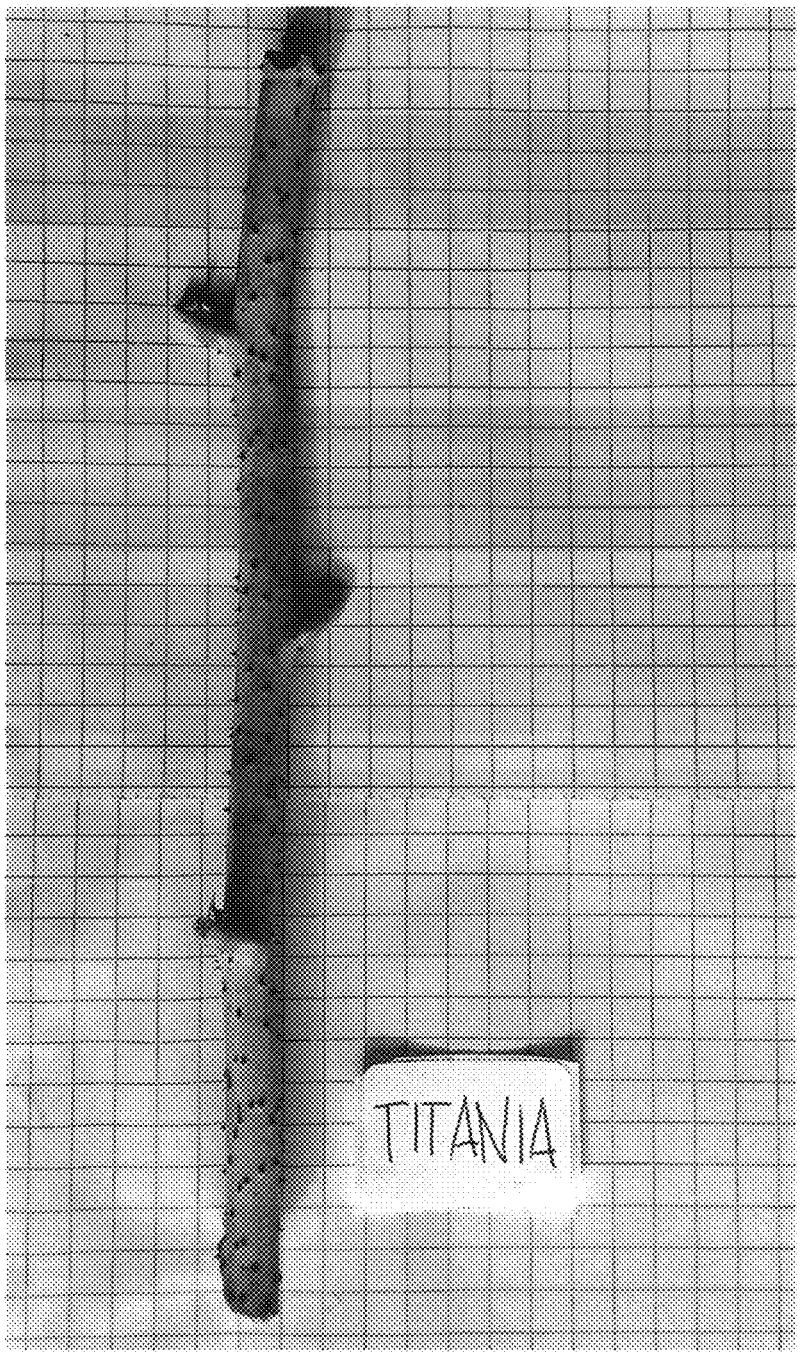
FIG. 3 is a view showing the plant primocane internode length, cane colour and thorns.
Figure 4:
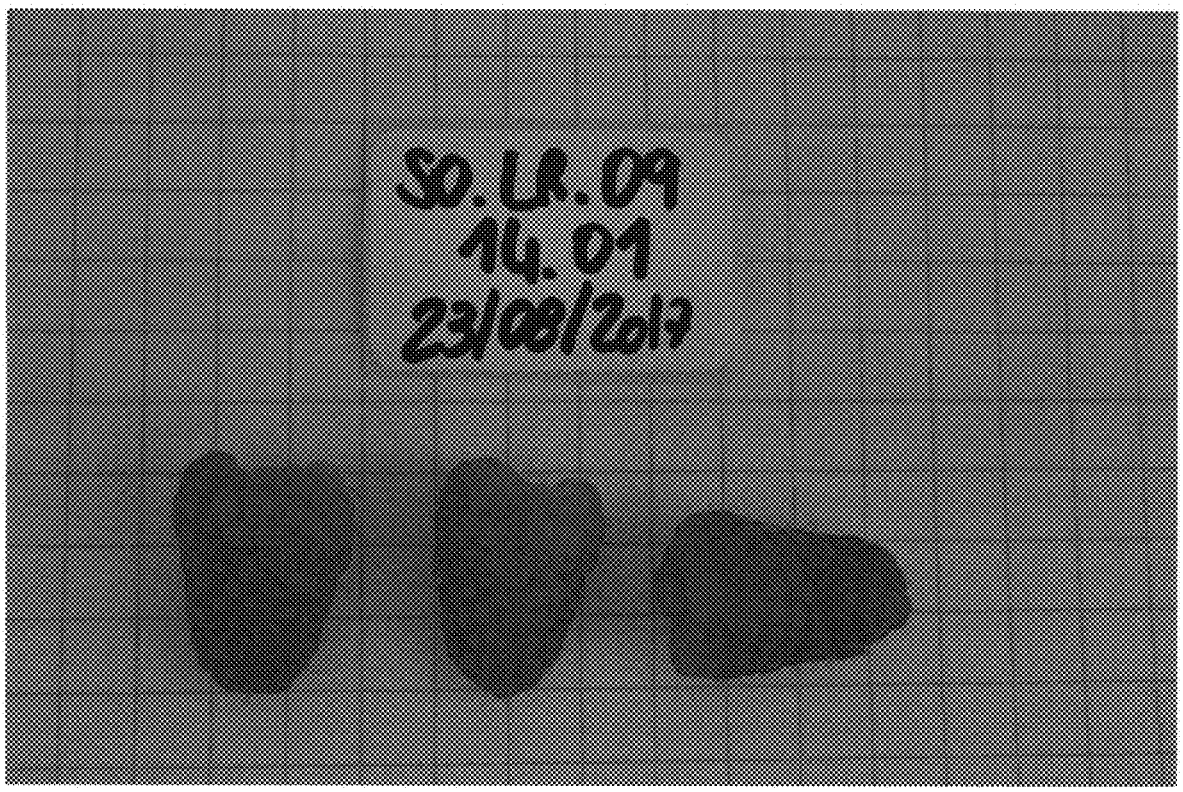
FIG. 4 is a view showing the ripe fruit size and shape.

The following detailed description set forth the distinctive characteristics of the new variety 'Titania'. The performance of the new cultivar for retention of its distinctive characteristics has been evaluated through successive asexual propagations by root cutting in the Applicant's setting at Altopiano della Vigolana, Trentino Region (Italy) under natural conditions in plastic covered high tunnel. The growing was in soilless conditions using coir as substrate.

* Colour references made to R.H.S. Colour Chart of The Royal Horticultural Society of London (Edition V)

The plant assessment was performed for 2 years. Botanical descriptions are for plants 4-6 months old.

Classification:

*Family*.—Rosaceae.

*Botanical*.—*Rubus idaeus* L.

*Common name*.—Raspberry.

Parentage: 'Vajolet Plus' x wild mountain raspberry plant.

Plant:

*General habit*.—Upright canes; very strong vigor; very good root system; adapted to medium winter chill conditions such as those at Altopiano della Vigolana (average min temperature 1° C.; average max temperature 5° C.); quite resilient to summer heat (average min temperature 13° C.; average max temperature 27° C.); high productivity in autumn.

*Average height* (*average*).—2.00-2.20 m.

*Spread* (*average*).—0.90 m.

*Shape*.—Vase.

*Vegetative bud length*.—Medium 4.0-6.0 mm.

Primocane:

*Length* (*average*).—2.0-2.20 m.

*Diameter* (*average*) *at* 1.0 *m height*.—1.1-1.2 cm.

*Texture*.—Smooth.

*Internode length* (*average*) *at* 1 *m height*.—Medium to long: 6.8-7.3 cm.

*Number of fruiting laterals per cane* (*average*).—9-10.

*Young shoot colour*.—* RHS: 140A.

*Cane colour*.—* RHS: 140B.

*Spines*.—Present/absent: present.

Spines:

*Shape*.—Narrow conical.

*Size* (*average*).—1.00-1.30 mm.

*Density* (*average*) *at* 1.2 *m height*.—3-4 per $cm^2$.

*Colour*.—* RHS 172A.

Foliage:

*Leaves*.—Shape: compound; odd-pinnate and subdivided in 3-5 ovate and serrate small leaflets. Predominant profile in cross section: flat. Rugosity: low. Complete leaf: Length: 32.4 cm. Width: 29.3 cm. Number of leaflets: 3-5. Upper surface colour: *RHS: 141B. Lower surface colour: *RHS 137D. Lateral leaflets: Specular. Lateral leaflets average size: Length:14.1 cm. Width: 9.5 cm. Lateral leaflets apex shape: pointed. Lateral leaflets base shape: ovate. Lateral leaflets margin type: serrate. Terminal leaflets average size: Length: 14.9 cm. Width: 11.0 cm. Terminal leaflets apex shape: pointed. Terminal leaflets base shape: slightly cordate. Terminal leaflets margin type: serrate.

*Petiole*.—Average length: 9.0 cm. Average diameter: 0.4 cm. Colour: *RHS 138C.

Inflorescence:

*Average length*.—63 cm.

*Average diameter*.—28.5 cm.

Flowers:

*Number per plant* (*average*).—213.

*Length* (*average*).—8.87 mm.

*Diameter* (*average*).—27.78 mm.

*Diameter* (*receptacle*).—7.75 mm.

*Shape*.—Pentagonal.

*Petal colour* (*upper surface*).—*RHS: NN155D.

*Petal colour* (*lower surface*).—*RHS: NN155D.

*Petal number* (*average*).—5.

*Petal shape*.—Obovate. Apex: rounded. Base: cuneate. Margin: entire.

*Sepal number* (*average*).—5. Colour (upper surface): *RHS: 144D. Colour (lower surface): *RHS: 142D. Length (average): 1.5 cm. Width (mid part): 0.6 cm.

*Fragrance*.—Absent.

*Blooming*.—July-August.

Fruit:

*Predominant shape*.—Conical.

*Weight*.—6.2 g.

*Size*.—Length: 3.0 cm. Width: 2.5 cm.

*Colour of ripe fruit*.—* RHS: 40B.

*Colour of immature fruit*.—*RHS: 39D.

*Firmness*.—Medium (0.04 Kg).

*Drupes per fruit* (*average*).—109.

*Drupe size*.—Length: 4.90 mm. Width: 4.46 mm. Depth: 6.49 mm.

*Glossiness*.—Medium to low.

*Adherence to plug*.—Medium.

*Titratable acidity*.—26.03 meq/hg.

*Soluble solids*.—8.3° Brix.

*Yield*.—4.9 kg linear/m (3 plants/m).

*Main bearing type*.—On current year's cane in autumn from half August to late October.

*Use/market*.—Suitable for consumption as high grade fresh fruit and also amenable to processing.

*Keeping quality*.—The fruit colour tends to become darker and soft during storage in case of late harvest.

*Storage capacity* (*shelf life*).—Good shelf-life.

*Shipping quality*.—Good; the attitude to storability permits shipping.

Reproductive organs:

*Pistil number per flower* (*average*).—120.

*Pistil size* (*average*).—5.17 mm.

*Stamen number per flower* (*average*).—95.

*Stamen size* (*average*).—5.07 mm.

Seeds:

*Size* (*average*).—Length: 3.90 mm. Width: 2.43 mm.

*Shape*.—Kidney-shaped.

Comparison with Commercial Cultivar

TABLE 1

Comparison table between variety and commercial cultivar 'Evita' (U.S. Plant Pat. No. 25,695)

| Characteristic | 'EVITA' | 'TITANIA' |
|---|---|---|
| fruit color | Orange red | Red |
| fruit size | Medium-large | Very large |
| plant vigor | vigorous | Very vigorous |
| Plant (size/vigour) | high | Very high |

TABLE 2

| Comparison table with female parental cultivar | | |
|---|---|---|
| Characteristic | 'VAJOLET PLUS' | 'TITANIA' |
| fruit color | Reddish orange | Red |
| Plant vigour | vigorous | Very very vigorous |
| Fruit: firmness | medium to firm | medium |
| Fruit size | Medium-large | Very large |

TABLE 2-continued

| Comparison table with female parental cultivar | | |
|---|---|---|
| Characteristic | 'VAJOLET PLUS' | 'TITANIA' |
| Fruit flavour | Very aromatic | Light aroma |
| Primocane yield | low | Very high |

What is claimed:

1. A new and distinct cultivar of raspberry plant as substantially herein shown and described.

* * * * *